US012667382B2

(12) United States Patent
Yao et al.

(10) Patent No.: US 12,667,382 B2
(45) Date of Patent: Jun. 30, 2026

(54) ULTRASONIC SCALPEL ROD TEMPERATURE CONTROL METHOD AND SYSTEM BASED ON TEMPERATURE DISTRIBUTION FUNCTION MODEL

(71) Applicant: Innolcon Medical Technology (Suzhou) Co., Ltd., Suzhou (CN)

(72) Inventors: Longyang Yao, Suzhou (CN); Fuyuan Wang, Suzhou (CN); Fei Ding, Suzhou (CN); Zhenzhong Liu, Suzhou (CN); Wei Luo, Suzhou (CN)

(73) Assignee: Innolcon Medical Technology (Suzhou) Co., Ltd., Suzhou (CN)

( * ) Notice: Subject to any disclaimer, the term of this patent is extended or adjusted under 35 U.S.C. 154(b) by 384 days.

(21) Appl. No.: 18/551,463

(22) PCT Filed: Apr. 15, 2022

(86) PCT No.: PCT/CN2022/087009
§ 371 (c)(1),
(2) Date: Sep. 20, 2023

(87) PCT Pub. No.: WO2023/029494
PCT Pub. Date: Mar. 9, 2023

(65) Prior Publication Data
US 2024/0164803 A1 May 23, 2024

(30) Foreign Application Priority Data
Aug. 30, 2021 (CN) .......................... 202111004178.X

(51) Int. Cl.
| A61B 17/32 | (2006.01) |
| A61B 17/00 | (2006.01) |
| G05D 23/19 | (2006.01) |

(52) U.S. Cl.
CPC . *A61B 17/320068* (2013.01); *G05D 23/1904* (2013.01); *G05D 23/1917* (2013.01); *A61B 2017/00017* (2013.01)

(58) Field of Classification Search
CPC .. A61B 17/320068; A61B 2017/00017; G05D 23/1904; G05D 23/1917
See application file for complete search history.

(56) References Cited

U.S. PATENT DOCUMENTS

| 2019/0274718 A1 | 9/2019 | Denzinger et al. |
| 2019/0282292 A1* | 9/2019 | Wiener .............. A61B 18/1233 |

FOREIGN PATENT DOCUMENTS

| CN | 103027748 | 4/2013 |
| CN | 104363849 | 2/2015 |
(Continued)

OTHER PUBLICATIONS

International Search Report corresponding to International Patent Application No. PCT/CN2022/087009, mailed Jun. 14, 2022 (6 pages).
(Continued)

*Primary Examiner* — Ashley L Fishback
(74) *Attorney, Agent, or Firm* — Armstrong Teasdale LLP

(57) ABSTRACT

The present invention discloses a temperature control method and a system for a blade shaft of an ultrasonic scalpel based on a temperature distribution function model. The system includes the blade shaft of the ultrasonic scalpel and a transducer that are coupled to each other, and is connected to a generator through a cable. When the blade shaft of the ultrasonic scalpel works, actual temperature of the blade shaft is distributed along a one-dimensional space of the blade shaft. The temperature distribution on the blade shaft is determined by a set of the real-time working feedback parameter, the physical structure feature parameter, and the surrounding environmental parameter of the
(Continued)

blade shaft. Each temperature distribution corresponds to a solution of the temperature distribution function, and the function can be approximated by a machine leaning algorithm. When the blade shaft of the ultrasonic scalpel works, the real-time temperature distribution of the blade shaft can be estimated by inputting, into a machine learning algorithm model, feature parameters such as the real-time resonance frequency, voltage, current, impedance, power, shape, and environment parameters of the blade shaft. Power control is performed based on the estimated temperature, which is accurate and effective.

16 Claims, 5 Drawing Sheets

(56)                References Cited

FOREIGN PATENT DOCUMENTS

| | | |
|---|---|---|
| CN | 111542281 | 8/2020 |
| CN | 111991058 | 11/2020 |
| CN | 113722994 | 11/2021 |
| CN | 113729864 | 12/2021 |
| CN | 113743007 | 12/2021 |
| EP | 3536262 A1 | 9/2019 |
| EP | 3616632 A1 | 3/2020 |

OTHER PUBLICATIONS

Supplementary European Search Report Issued for Application No. 22862640.4 on Mar. 11, 2025 (20 pages).

* cited by examiner

ULTRASONIC SCALPEL ROD TEMPERATURE CONTROL METHOD AND SYSTEM BASED ON TEMPERATURE DISTRIBUTION FUNCTION MODEL

CROSS-REFERENCE TO RELATED APPLICATIONS

This application is a U.S. National Phase Application of International Patent Application No. PCT/CN22/87009, filed Apr. 15, 2022, which claims priority to Chinese Patent Application No. 202111004178.X, filed Aug. 30, 2021, each of which is hereby incorporated by reference herein.

FIELD OF THE INVENTION

The present invention relates to the field of medical instrument, particularly to a control method and a system for an ultrasonic scalpel, and more particularly, to a temperature control method and a system for a blade shaft of an ultrasonic scalpel based on a temperature distribution function model, and a generator, an ultrasonic scalpel surgical instrument, and an ultrasonic scalpel system provided with the system.

BACKGROUND OF THE INVENTION

An ultrasonic cutting and hemostasis surgical system (referred to as an ultrasonic scalpel system for short) for soft tissue refers to an instrument that further amplifies ultrasonic vibration obtained by a piezoelectric converter (the electric energy is transmitted to the piezoelectric converter by an energy generator, which converts the electrical energy into mechanical energy), and uses the amplified ultrasonic vibration by the blade shaft of the ultrasonic scalpel to cut and coagulate soft tissue. Clinical use of this instrument can achieve lesion resection at lower temperatures with less bleeding and ensure minimal lateral thermal damages to the tissue. With the popularization of minimally invasive surgery, the ultrasonic scalpel has become a regular surgical instrument.

The ultrasonic scalpel system mainly includes a generator, a transducer, and an ultrasonic scalpel blade shaft. As shown in FIG. 1, the transducer 11 of an ultrasound scalpel is matched with a housing 12 of the ultrasound scalpel. A sleeve 13 is located at a distal end of the housing 12 of the ultrasound scalpel, and an ultrasonic scalpel blade shaft 14 at a farthest end is coupled to the transducer 11 within the sleeve 13. The transducer 11 is connected to a generator (not shown) through a cable 15. The current for ultrasonic frequency in the generator is transmitted to the transducer. The transducer converts electrical energy into mechanical energy for front and rear vibration, and enables, through transmission and amplification of the ultrasonic scalpel blade shaft, the tip of the blade shaft (also referred to as cutter head) of the ultrasonic scalpel to vibrate at a certain frequency (for example, 55.6 kHz). Due to the heat generated by friction, the water in tissue cells in contact with the blade tip vaporizes, hydrogen bonds of the protein break, the cells disintegrate and recombine, and the tissue is cut after coagulation. When cutting a blood vessel, the blade shaft of the ultrasonic scalpel is in contact with the proteins of the tissue. Heat is generated through mechanical vibration, which results in destruction of the collagen structure in the tissue. As a result, protein coagulation is produced, the blood vessel is sealed, and the objective of hemostasis is achieved.

Due to a rapid thermal effect during surgery, the cutter head of the ultrasonic scalpel blade shaft can form a local high-temperature area above 300° C. in a short period of time. Heat is mainly diffused through the ultrasonic scalpel blade shaft, the tissue, and air. An excessively high temperature of the cutter head of the ultrasonic scalpel can accelerate loss of the cutter head, especially a gasket, and may cause thermal damage to surrounding tissues, which is adverse to wound recovery and may even cause various complications. An excessively low temperature of the cutter head of the ultrasonic scalpel may lead to excessively slow cutting, which seriously reduces the efficiency of the surgeon during an operation.

Chinese patent CN111542281A discloses a method for determining the temperature of an ultrasonic scalpel. The temperature of the ultrasonic scalpel is inferred by the difference between an actual resonance frequency and a reference resonance frequency of the ultrasonic electrical system. Shortcomings of this method are as follows. First, reference resonance frequencies of different scalpels are significantly different, and may vary with loss of the scalpels and environmental conditions. This patent does not reflect how the reference resonance frequency varies with the working state and other feature parameters. Therefore, it is not accurate enough to infer the temperature of the ultrasonic scalpel based on the difference between an actual reference resonance frequency and the reference resonance frequency. In addition, in practical work, the impact on the working state of the ultrasonic scalpel is a complex state function, and the phase difference is only a direct factor affecting the real-time resonance frequency. The real-time working state and temperature of the ultrasonic scalpel may be affected by many other features, such as the voltage, current and power in the real-time working; characteristics of the physical material of the blade shaft, the length of the blade shaft, the shape, and the impedance; and environmental factors such as temperature and humidity. These states should be directly considered in the temperature distribution function model to obtain a relatively accurate real-time temperature distribution.

SUMMARY OF THE INVENTION

To resolve the foregoing problems in the prior art, the present invention provides a temperature control method and system for a blade shaft of an ultrasonic scalpel based on a temperature distribution function model, and a generator, an ultrasonic scalpel surgical instrument, and an ultrasonic scalpel system provided with the system.

To resolve the foregoing technical problems, the present invention provides the following technical solutions.

A temperature control method for a blade shaft of an ultrasonic scalpel based on a temperature distribution function model, including the following steps:

S1) saving the temperature distribution function model and at least one threshold value;

S2) inputting a corresponding input feature to the temperature distribution function model, and outputting corresponding temperature data information;

S3) comparing at least one value in the temperature data information with the threshold value; and S4) adjusting, based on the comparison result, a power level applied to an ultrasonic-scalpel transducer to modulate the temperature of the ultrasonic scalpel blade.

Preferably, the temperature distribution function model is a neural network algorithm model, including one or a combination of more than one algorithm models of a feed-forward neural network, a memory neural network, and an attention neural network; and the training method for the model is one or a combination of more than one of a supervised learning, a semi-supervised learning, an unsupervised learning, and a reinforcement learning.

Preferably, the training method for the model specifically comprises: extracting an input feature from a training set, and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing processes until the model meets a predetermined stop condition; and stopping training and saving the model after the stop condition is met.

Preferably, the input feature of the temperature distribution function model includes one or a combination of more than one of a working feedback parameter, a physical structure feature parameter, and an environmental parameter.

Preferably, the working feedback parameter includes, but is not limited to a real-time voltage U, a real-time current I, a power P, an impedance R, and a real-time response frequency f; the physical structure feature parameter includes, but is not limited to a material of the blade shaft of the ultrasonic scalpel, and a length of the blade shaft; and the environmental parameter includes, but is not limited to an environmental temperature, and an environmental humidity.

Preferably, the temperature data information includes a real-time temperature value at any point on the blade shaft of the ultrasonic scalpel, and/or a maximum temperature value, a minimum temperature value, and an average temperature of a certain area on the blade shaft of the ultrasonic scalpel.

Preferably, the temperature distribution function model consists of layers, corresponding neurons, and weights; wherein weight parameters and application programs are saved in a memory of the generator; the memory comprises a flash, an EEPROM, or another non-volatile storage device; the application program runs in a processor; and the processor comprises an ARM, a DSP, a FPGA, a CPU, a GPU, or an ASI chip existing in the generator, or is a remote server connected through a network.

Preferably, in step S2, the output temperature data information forms a one-dimensional spatial temperature distribution T(l) along the blade shaft of the ultrasonic scalpel, which is a solution of an equation $$\frac{n}{2f} = \int_0^L \frac{1}{V(T(l))} dl.$$

The present invention further discloses a temperature control system for the blade shaft of the ultrasonic scalpel based on the temperature distribution function model, including:
a storage unit, configured to save the temperature distribution function model and at least one threshold value;
a processing unit, configured to input a corresponding input feature to the temperature distribution function model, and output corresponding temperature data information;
a comparison unit, configured to compare at least one value in the temperature data information with the threshold value; and an adjusting unit, configured to adjust, based on the comparison result, the power level applied to the transducer of the ultrasonic scalpel to modulate the temperature of the blade shaft of the ultrasonic scalpel.

The present invention further discloses a generator for temperature control based on the temperature distribution function model, including:
a control circuit coupled to a memory, wherein the control circuit is configured to be able to:
save the temperature distribution function model and at least one threshold value;
input a corresponding input feature to the temperature distribution function model, and output corresponding temperature data information;
compare at least one value in the temperature data information with the threshold value; and
adjust, based on the comparison result, the power level applied to the transducer of the ultrasonic scalpel to modulate the temperature of blade shaft of the ultrasonic scalpel.

Preferably, the control circuit is configured that the input feature input to the temperature distribution function model includes one or a combination of more than one of a working feedback parameter, a physical structure feature parameter, and an environmental parameter.

Preferably, the working feedback parameter includes, but is not limited to a real-time voltage U, a real-time current I, a power P, an impedance R, and a real-time response frequency f; the physical structure feature parameter includes, but is not limited to a material of the blade shaft of the ultrasonic scalpel, and a length of the blade shaft; and the environmental parameter includes, but is not limited to an environmental temperature, and an environmental humidity.

Preferably, the temperature data information includes a real-time temperature value at any point on the blade shaft of the ultrasonic scalpel, and/or a maximum temperature value, a minimum temperature value, and an average temperature of a certain area on the blade shaft of the ultrasonic scalpel.

The present invention further discloses an ultrasonic scalpel surgical instrument based on the temperature distribution function model, including:
an ultrasonic electromechanical system, including an ultrasonic transducer connected to an ultrasonic scalpel through an ultrasonic waveguide; and
a generator, configured to supply power to the ultrasonic transducer, wherein the generator includes a control circuit configured to be able to:
save the temperature distribution function model and at least one threshold value;
input a corresponding input feature to the temperature distribution function model, and output corresponding temperature data information;
compare at least one value in the temperature data information with the threshold value; and
adjust, based on the comparison result, the power level applied to the transducer of the ultrasonic scalpel to modulate the temperature of the blade shaft of the ultrasonic scalpel.

Preferably, the control circuit is configured that the input feature input to the temperature distribution function model includes one or a combination of more than one of a working feedback parameter, a physical structure feature parameter, and an environmental parameter; wherein the working feedback parameter includes, but is not limited to a real-time voltage U, a real-time current I, a power P, an impedance R, and a real-time response frequency f; the physical structure feature parameter includes, but is not limited to a material of the blade shaft of the ultrasonic scalpel, and a length of the blade shaft; and the environmental parameter includes, but is not limited to an environmental temperature, and an environmental humidity.

Preferably, the temperature data information includes a real-time temperature value at any point on the blade shaft of the ultrasonic scalpel, and/or a maximum temperature value, a minimum temperature value, and an average temperature of a certain area on the blade shaft of the ultrasonic scalpel.

The present invention further discloses an ultrasonic scalpel system based on the temperature distribution function model, including a processor and a non-volatile storage device including an application program, wherein the application program, when executed by the processor, enables the processor to:

save the temperature distribution function model and at least one threshold value;

input a corresponding input feature to the temperature distribution function model, and output corresponding temperature data information;

compare at least one value in the temperature data information with the threshold value; and adjust, based on the comparison result, the power level applied to the transducer of the ultrasonic scalpel to modulate the temperature of the blade shaft of the ultrasonic scalpel.

Preferably, the temperature distribution function model consists of layers, corresponding neurons, and weights; wherein weight parameters and an application program are saved in a memory of the generator; the memory comprises a flash, an EEPROM, or another non-volatile storage device; the application program runs in a processor; and the processor comprises an ARM, a DSP, a FPGA, a CPU, a GPU, or an ASIC chip existing in the generator, or is a remote server connected through a network.

Beneficial effects of the present invention mainly are as follows. When the blade shaft of the ultrasonic scalpel works, the actual temperature of the blade shaft is distributed along a one-dimensional space of the blade shaft. The temperature distribution on the blade shaft is determined by a set of the real-time working feedback parameter, the physical structure feature parameter, and the surrounding environmental parameter of the blade shaft of the ultrasonic scalpel. Each temperature distribution corresponds to a solution of the temperature distribution function, and the function can be approximated by a machine leaning algorithm. When the blade shaft of the ultrasonic scalpel works, the real-time temperature distribution of the blade shaft of the ultrasonic scalpel can be estimated by inputting, into a machine learning algorithm model, the feature parameters such as the real-time resonance frequency, the voltage, the current, the impedance, the power and the shape of the blade shaft of the ultrasonic scalpel, and the environment. Further, the power control is performed based on the estimated temperature, which is accurate and effective.

6

Figure 5:
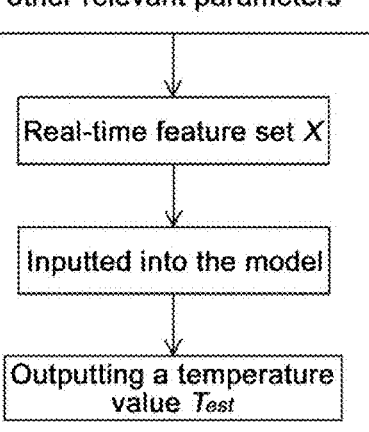
Figure 6:
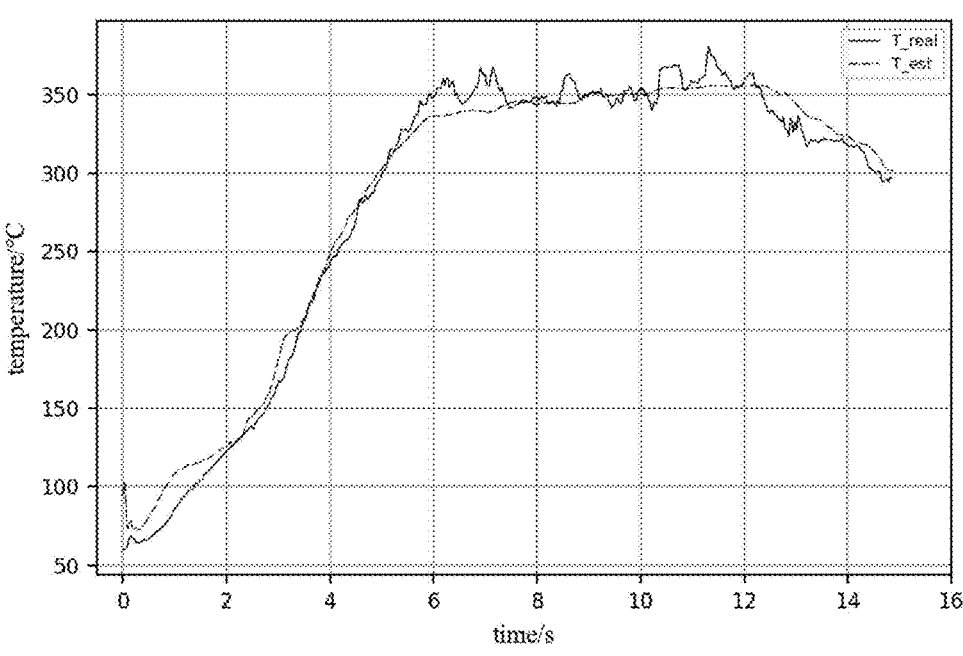
Figure 7:
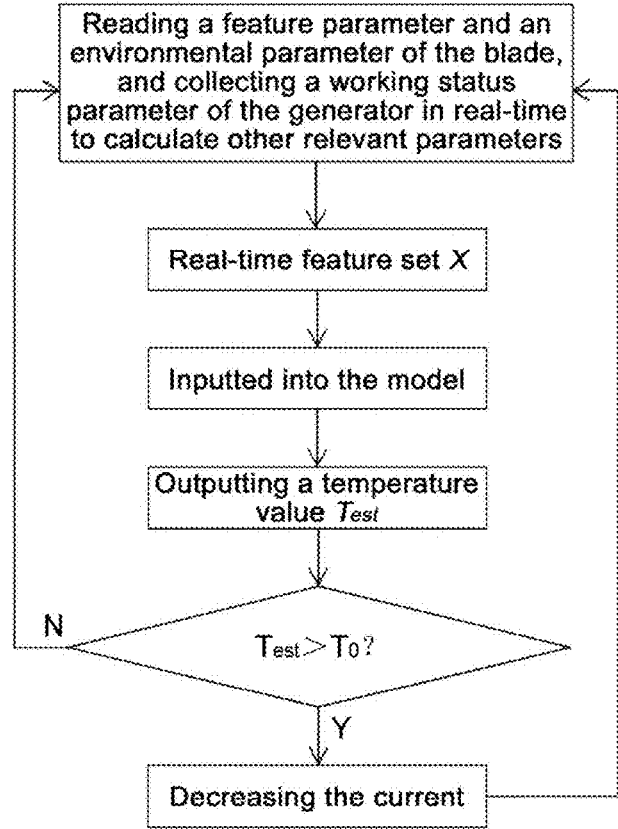
Figure 8:
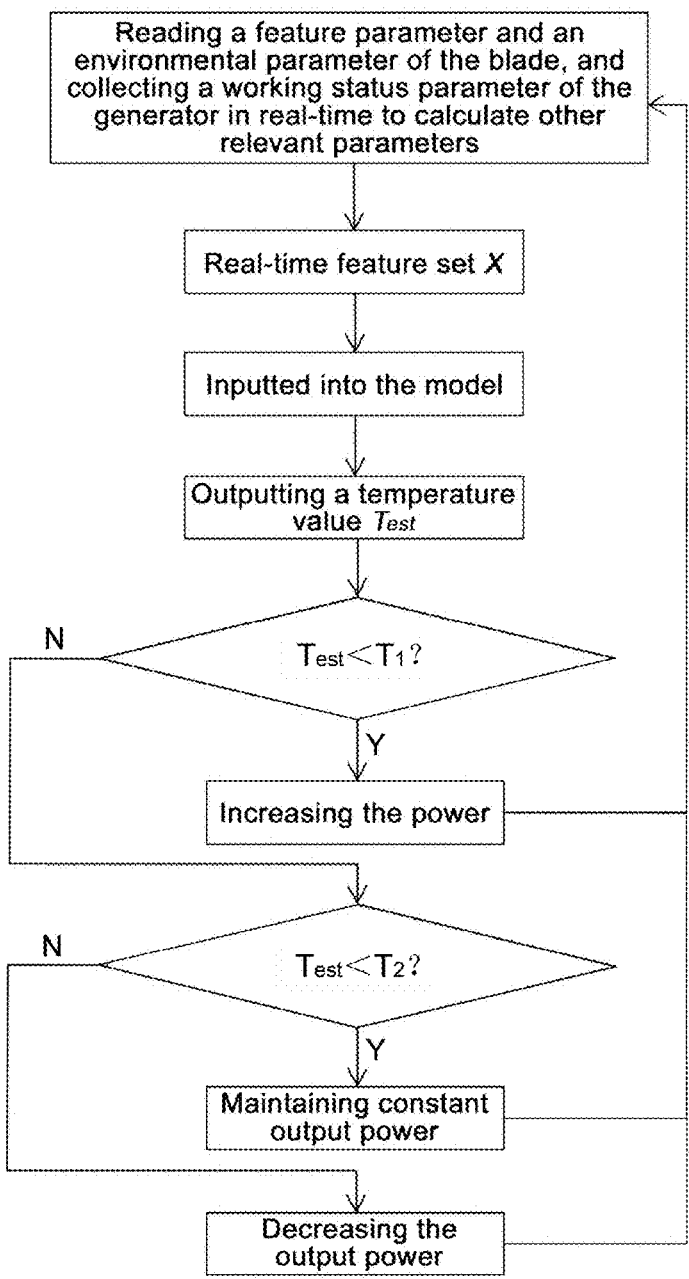
Figure 9:
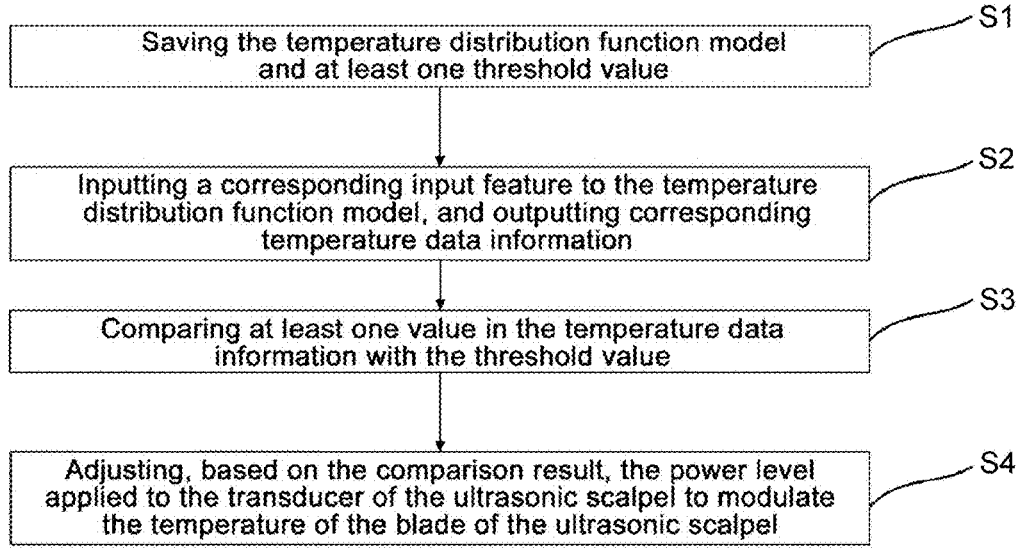

FIG. 5 is a flowchart of predicting the temperature based on the temperature distribution function model according to the present invention;

FIG. 6 is a comparison diagram of the temperature predicted based on the temperature distribution function model and the actual temperature according to the present invention;

FIG. 7 is a flowchart of predicting the temperature based on the temperature distribution function model according to a first embodiment of the present invention;

FIG. 8 is a flowchart of predicting the temperature based on the temperature distribution function model according to a second embodiment of the present invention; and FIG. 9 is a flowchart of performing subsequent control based on the temperature predicted based on the temperature distribution function model according to the present invention.

DETAILED DESCRIPTION OF THE EMBODIMENTS

The present invention will be described in detail below with reference to specific implementations shown in the accompanying drawings. However, the present invention is not limited to these implementations, and modifications in structure, method, or function that are made by persons of ordinary skills in the art based on these implementations all fall within the protection scope of the present invention.

The ultrasonic scalpel system uses a phase-locked algorithm to change the operating frequency of the transducer during operation, so that the transducer operates in a state with maximum efficiency, that is, a resonant state. In the resonant state, propagation of the sound wave on the blade shaft of the ultrasonic scalpel needs to meet a standing wave condition. Assuming that the length of the blade shaft of the ultrasonic scalpel is L, the wavelength of the sound wave is $\lambda$, the sound velocity is v, and the response frequency is f, the following operating condition needs to be met in the resonant state:

$$n = 2\frac{L}{\lambda}, \tag{1}$$

wherein n is a positive integer.

Assuming that the period of the sound wave is t, the following formula is met:

$$\tau = \frac{\lambda}{v} = \frac{1}{f}. \tag{2}$$

It can be obtained that:

$$\lambda = \frac{v}{f}. \tag{3}$$

In actual operation, the heat diffuses along a set direction of the blade shaft of the ultrasonic scalpel, and therefore the temperature may vary at different positions of the blade shaft of the ultrasonic scalpel. The temperature t at different positions is expressed as:

$$t = T(l), \tag{4}$$

wherein T(l) is a temperature distribution function at a position on the blade shaft, l is in the range of 0~L, and a vertex position on one side of the blade tip of the blade shaft is a coordinate origin.

Temperature may affect Young's modulus of the blade shaft, and finally affect the sound velocity. The sound velocity v at different positions on the scalpel blade can be expressed as a function of temperature:

$$v(l) = V(T(l)). \tag{5}$$

The formula (1) can be expressed as:

$$n = 2\int_0^L \frac{1}{\lambda(l)}dl = 2f \times \int_0^L \frac{1}{V(T(l))}dl. \tag{6}$$

The formula (6) can be expressed as:

$$\frac{n}{2f} = \int_0^L \frac{1}{V(T(l))}dl. \tag{7}$$

The formula (7) is an integral equation. For a determined time point, f is a determined response frequency, and the temperature T(l) is affected by parameters such as voltage, current, power, impedance, the shape of the blade shaft, and environmental parameters. When n, f, and L are determined, the temperature distribution function T(l) of the integral equation may have infinite solutions. For different blade shafts, there may be more different temperature distributions.

In view of the above, the present invention discloses a machine learning algorithm model, specifically a neural network algorithm model. An artificial neural network algorithm model is a mathematical model inspired by the human brain and nervous system. Similar to biological neurons, the artificial neural network algorithm model is composed of a plurality of nodes (artificial neurons) that are connected to each other, and can be used to model a complex relationship between data. Connections between different nodes are assigned with different weights, and each weight represents an impact level of one node on another node. Each node represents a specific function. Information from another node is comprehensively calculated based on the corresponding weight of the node, and is input into an activation function to obtain a new activation value. The activation function is used to introduce a nonlinear element and improve the expression capability of the neural network. Common activation functions include Sigmaid, Tanh, ReLU, and the like.

From a system perspective, the artificial neuron is an adaptive nonlinear dynamic system composed of a large quantity of neurons connected through extremely rich and complete connections. A most commonly used neural network learning algorithm for the moment is the back propagation algorithm, and an optimization method is the gradient descent algorithm. Theoretically, any function can be approximated through a two-layer neural network. Increase of the quantity of network layers can make the neural network have stronger representation capability under the same quantity of neurons. Currently, commonly used neural network models include the feedforward neural network model, the memory neural network model, the attention neural network model, and the like. The multilayer perceptron (MLP) and the convolutional neural network (CNN) are feedforward neural network models. The recurrent neural network (RNN) is a memory neural network model. Commonly used RNN models include the gate recurrent unit (GRU) and the long short-term memory network (LSTM). The attention neural network model includes a transformer and the like.

Figure 1:
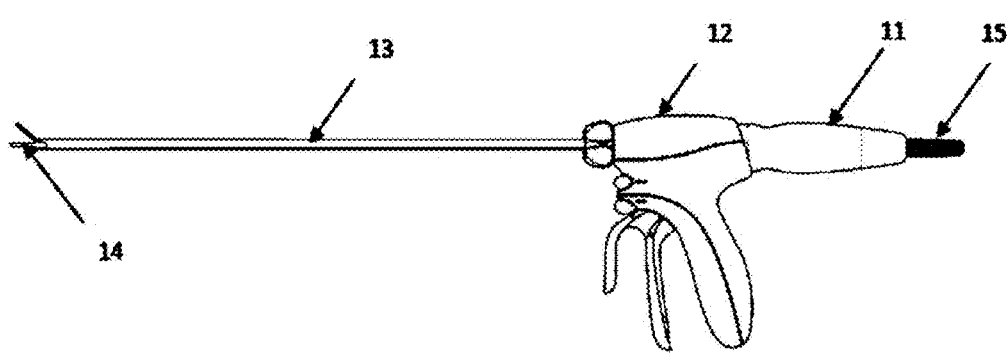
FIG. 1 is a diagram of the structural configuration of the ultrasonic scalpel in the prior art.
Figure 2:
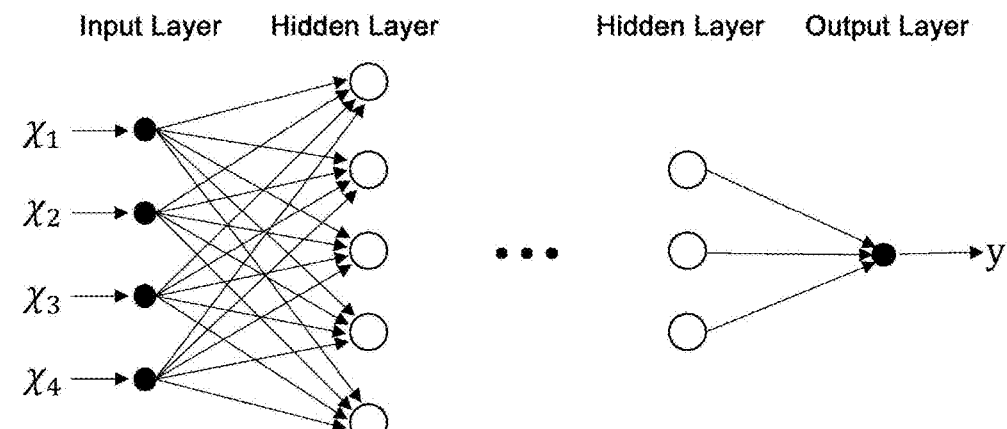
FIG. 2 is a structural diagram of a typical multilayer feedforward neural network.

A typical multilayer feedforward neural network model is shown in FIG. 2, which includes an input layer, several hidden layers, and one output layer. Input information X is propagated forward through each layer to finally obtain an output y.

The information propagation formula on each layer is:

$$a^l = f_l\big(W^l a^{l-1} + b^l\big), \tag{8}$$

wherein $a^{l-1}$ represents input of an $l^{th}$ layer, a' represents output of the $l^{th}$ layer, $f_l$ represents an activation function of a neuron on the $l^{th}$ layer, $W^l$ represents a weight matrix from a $(l-1)^{th}$ layer to the $l^{th}$ layer, and $b^l$ represents an offset from the $(l-1)^{th}$ layer to the $l^{th}$ layer.

On the basis of the feedforward neural network, the memory neural network model is added with a memory capability, which is generally used to process time series data. Commonly used memory neural networks include RNN, GRU, LSTM, and the like. The GRU and the LSTM have long-term memory capabilities and can process long-time sequences.

Figure 3:
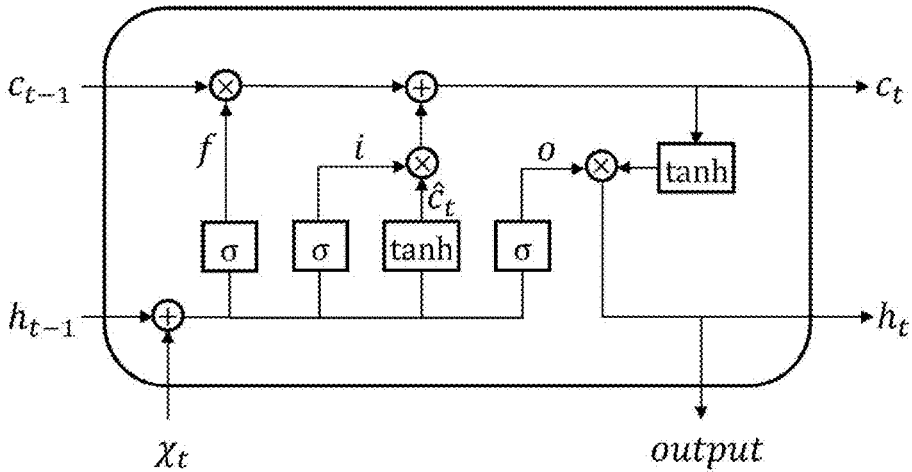
FIG. 3 is a structural diagram of a LSTM gated neuron.

A gating neuron structure of a typical long short-term memory (LSTM) neural network model is shown in FIG. 3. The neuron of the LSTM controls the path for information transmission through a gating mechanism. Three gates respectively are an input gate i, a forget gate f, and an output gate o. Functions of the three gates are as follows: the input gate i controls the quantity of candidate states $\hat{C}_t$ that need to be saved at a current moment; the forget gate f controls the amount of information that needs to be forgotten in an internal state $c_{t-1}$ at a previous moment; and the output gate o controls the amount of information that needs to be output to an external state $h_t$ in an internal state $c_t$ at the current moment. Through a LSTM recurrent unit, a long-distance time sequence dependency can be established in the entire neural network.

The three gates respectively are:

$$i = \sigma(W_i[h_{t-1}, \chi_t] + b_i); \tag{9}$$

$$f = \sigma(W_f[h_{t-1}, \chi_t] + b_f); \tag{10}$$

$$o = \sigma(W_o[h_{t-1}, \chi_t] + b_o). \tag{11}$$

Formulas for updating the internal states are:

$$\hat{c}_t = \tanh(W_c[h_{t-1}, \chi_t] + b_c); \tag{12}$$

$$c_t = f \odot c_{t-1} + i \odot \hat{c}_t; \tag{13}$$

$$h_t = o \odot \tanh(c_t). \tag{14}$$

The temperature distribution function model in the present invention can be based on a machine learning algorithm model, and includes one or a combination of more than one algorithm models. The input feature includes one or a combination of more than one of a working feedback parameter, a physical structure feature parameter, and an environmental parameter. The working feedback parameter includes, but is not limited to the real-time voltage U, the real-time current I, the power P, the impedance R, and the real-time response frequency f. The physical structure feature parameter includes, but is not limited to the material and the length of the blade shaft of the ultrasonic scalpel. The environmental parameter includes, but is not limited to the environmental temperature and the environmental humidity.

A more complete input feature indicates a stronger approximation capability of the neural network model. In the model of the present invention, the voltage U and the current I are obtained through real-time sampling by the generator, and the real-time power P and the impedance R can be calculated according to the following formulas:

$$P = U \times I; \text{ and} \tag{15}$$

$$R = \frac{U}{I}. \tag{16}$$

The real-time frequency f is calculated according to the following formula:

$$f = k \times (\theta - \theta_0), \tag{17}$$

wherein k is determined by a functional relationship between the real-time voltage U and the current I:

$$k = K(U, I). \tag{18}$$

The physical structure feature parameters, such as the material and the length, of the blade shaft of the ultrasonic scalpel can be saved in a memory chip of the ultrasonic scalpel or the generator. The generator can directly read the corresponding memory chip to obtain these feature parameters. The environmental parameter can be measured in a real-time manner by a sensor.

The temperature distribution function model of the present invention can simultaneously estimate one or more temperature data information, including but not limited to a real-time temperature value at any point on the blade shaft of the ultrasonic scalpel, and/or a maximum temperature value, a minimum temperature value, and an average temperature of a certain area on the blade shaft of the ultrasonic scalpel.

The model training method of the present invention comprises supervised learning, semi-supervised learning, unsupervised learning, or reinforcement learning etc. Regarding the supervised learning, all input feature information and training labels of the model need to be collected at a certain time interval, wherein the time interval may be 1 ms or 10 ms; and real-time temperature is measured to serve as a supervision training label. The real-time temperature at cutting point can be measured by an embedded or external temperature sensor or an infrared thermometer. A large amount of marked data is collected to obtain a training dataset S.

Figure 4:
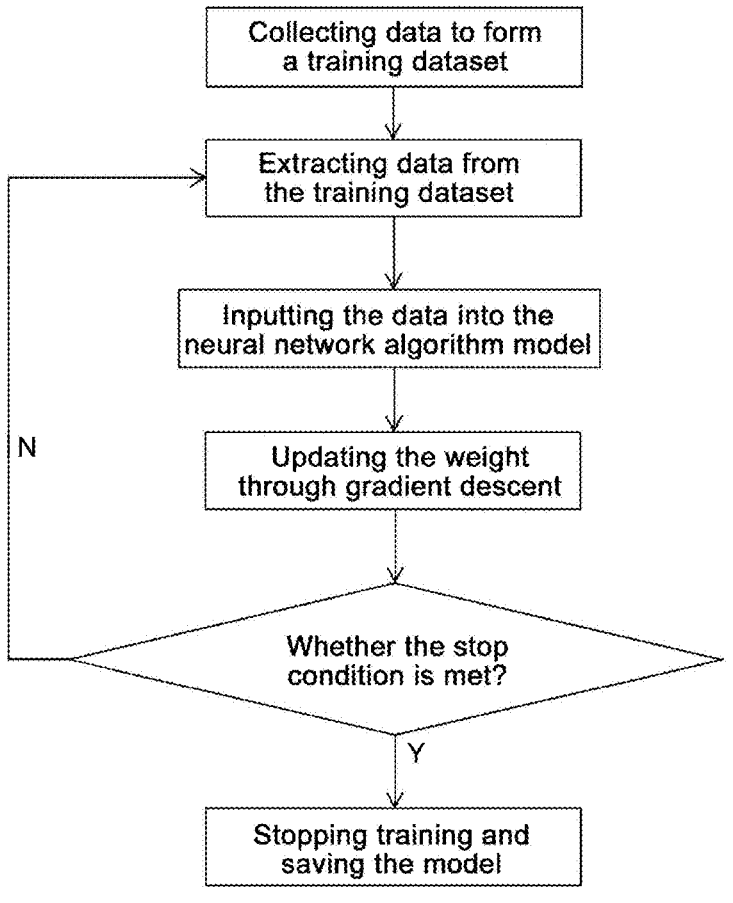
FIG. 4 is a diagram of a model establishment, training, and saving method according to the present invention.

A training process of the neural network model implemented through the supervised learning of the model is shown in FIG. 4. The input feature is extracted from the training dataset S, and is input into the neural network model to calculate an intermediate value and a gradient value for each neuron. A loss function of the model may be a mean square error MSE or an average absolute error MAE. The weight is updated by a gradient descent method. The foregoing process is repeated until the model meets a predetermined stop condition, for example, the prediction accuracy reaches a target value or the losses no longer decrease. After the stop condition is met, the training is stopped and the model is saved. This model can represent a function of temperature distribution on the blade shaft, including the blade tip, during the operation of all target ultrasonic scalpels.

The trained model consists of various layers, corresponding neurons, and the weights. The weight parameters and the application algorithm programs are saved in a memory of the generator. The memory may be a Flash, an EEPROM, or another non-volatile storage device. The application program runs in a processor. The processor may be an ARM, a DSP, a FPGA, a CPU, a GPU, or an ASIC chip existing in the generator, or may be a remote server connected via a network.

A temperature estimation method using the temperature distribution function model of the present invention is shown in FIG. 5. A real-time feature parameter set X of the ultrasonic scalpel is input into the model, and the model can find most probable temperature distribution of the blade shaft based on the input feature set. The target temperature Test can be obtained from the temperature distribution, and Test is a real-time target temperature value.

As shown in FIG. 6, the curve in the figure is a temperature change curve of an ultrasonic scalpel when it is used to cut cattlehide. The solid line represents an actual temperature, and the actual temperature is measured by an infrared thermometer in a real-time manner. The dashed line represents a real-time estimated temperature of the model. The real-time temperature is estimated every 10 ms, with a total of approximately 1500 temperature prediction points. The temperature prediction range is 60-350° C. It can be seen that the model can accurately predict the temperature value, and there may be small temperature deviations only at the cutting start point and nearby a point of 350° C.

According to the present invention, the temperature control method for the blade shaft of the ultrasonic scalpel based on the temperature distribution function model is to control the output energy of the ultrasonic scalpel based on the predicted real-time temperature. As shown in FIG. 9, the method specifically includes the following steps:

inputting a corresponding input feature to the temperature distribution function model, and outputting corresponding temperature data information;

comparing at least one value in the temperature data information with a threshold value; and adjusting, based on the comparison result, the power level applied to the transducer of the ultrasonic scalpel to modulate the temperature of the blade shaft of the ultrasonic scalpel.

One implementation is shown in FIG. 7. A temperature threshold $T_0$ is preset, wherein $T_0$ can correspond to a high-temperature threshold value. When the predicted real-time temperature exceeds the threshold value, the output power can be reduced by gradually decreasing the voltage or the current, thereby effectively reducing the temperature. A method of reducing the power is to reduce the current by 5% every 200 ms. The power may be adjusted to increase, decrease, or remain unchanged. Power adjustment can be implemented by adjusting an output voltage or current, and the time interval and the amplitude value for adjustment may not be limited to present values. The power adjustment threshold value can include a plurality of temperature threshold values, and the temperature threshold values can be any temperature within 0-600° C.

Another implementation is shown in FIG. 8. The control method includes a first temperature threshold value $T_1$ and a second temperature threshold value $T_2$. The output power is increased when the predicted real-time temperature is lower than the first temperature threshold value $T_1$. The power is kept constant when the temperature is between the first temperature threshold value $T_1$ and the second temperature threshold value $T_2$. The power is decreased when the temperature is higher than the second temperature threshold value $T_2$. The output power control method is not limited to the foregoing control method, which can also be another control method that complies with the control framework.

The present invention further discloses a generator, including:

a control circuit coupled to a memory, wherein the control circuit is configured to be able to:

save a temperature distribution function model and at least one threshold value;

input a corresponding input feature to the temperature distribution function model, and output corresponding temperature data information;

compare at least one value in the temperature data information with the threshold value; and adjust, based on the comparison result, the power level applied to a transducer of the ultrasonic scalpel to modulate the temperature of the blade shaft of the ultrasonic scalpel.

The present invention further discloses an ultrasonic scalpel surgical instrument, including:

an ultrasonic electromechanical system, including an ultrasonic transducer connected to the ultrasonic scalpel through an ultrasonic waveguide; and a generator, configured to supply power to the ultrasonic transducer, wherein the generator includes a control circuit configured to be able to:

save a temperature distribution function model and at least one threshold value;

input a corresponding input feature to the temperature distribution function model, and output corresponding temperature data information;

compare at least one value in the temperature data information with the threshold value; and adjust, based on the comparison result, the power level applied to the transducer of the ultrasonic scalpel to modulate the temperature of the blade shaft of the ultrasonic scalpel.

The present invention further discloses an ultrasonic scalpel system, including a processor and a non-volatile storage device including an application program, wherein the application program, when executed by the processor, enables the processor to: save a temperature distribution function model and at least one threshold value;

input a corresponding input feature to the temperature distribution function model, and output corresponding temperature data information;

compare at least one value in the temperature data information with the threshold value; and adjust, based on the comparison result, the power level applied to the transducer of the ultrasonic scalpel to modulate the temperature of the blade shaft of the ultrasonic scalpel.

The foregoing descriptions are merely preferred implementations of the present invention. It should be pointed out that the foregoing preferred implementations should not be considered as limitation to the present invention, and the protection scope of the present invention should be subject to the scope defined in the claims. For persons of ordinary skills in the art, improvements and modifications can also be made without departing from the spirit and the scope of the present invention. These improvements and modifications should also be considered to fall within the scope of the present invention.

What is claimed is:

1. A temperature control method for a blade shaft of an ultrasonic scalpel based on a temperature distribution function model, comprising the following steps:

saving the temperature distribution function model and at least one threshold value;

inputting a corresponding input feature to the temperature distribution function model, and outputting corresponding temperature data information;

comparing at least one value in the temperature data information with the threshold value; and adjusting, based on the comparison result, a power level applied to a transducer of the ultrasonic scalpel to modulate a temperature of the blade shaft of the ultrasonic scalpel, wherein the temperature distribution function model is a neural network algorithm model, comprising one or a combination of more than one algorithm models of a feedforward neural network, a memory neural network, and an attention neural network; and a training method for the model is one or a combination of more than one of a supervised learning, a semi-supervised learning, an unsupervised learning, and a reinforcement learning, and wherein the training method for the model specifically comprises: extracting an input feature from a training set and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing process until the model meets a predetermined stop condition; and stopping training and saving the model after the stop condition is met.

2. The method according to claim 1, wherein the input feature of the temperature distribution function model comprises one or a combination of more than one of a working feedback parameter, a physical structure feature parameter, and an environmental parameter.

3. The method according to claim 2, wherein the working feedback parameter comprises, but is not limited to a real-time voltage U, a real-time current I, a power P, an impedance R, and a real-time response frequency f; the physical structure feature parameter comprises, but is not limited to a material of the blade shaft of the ultrasonic scalpel, and a length of the blade shaft; and the environmental parameter comprises, but is not limited to an environmental temperature, and an environmental humidity.

4. The method according to claim 1, wherein the temperature data information comprises a real-time temperature value at any point on the blade shaft of the ultrasonic scalpel, and/or a maximum temperature value, a minimum temperature value, and an average temperature of a certain area on the blade shaft of the ultrasonic scalpel.

5. The method according to claim 1, wherein the temperature distribution function model consists of layers, corresponding neurons, and weights; wherein weight parameters and application programs are saved in a memory of a generator; the memory comprises a flash, an EEPROM, or another non-volatile storage device; the application program runs in a processor; and the processor comprises an ARM, a DSP, a FPGA, a CPU, a GPU, or an ASIC chip existing in the generator, or is a remote server connected through a network.

6. The method according to claim 1, wherein said outputting corresponding temperature data information forms a one-dimensional spatial temperature distribution T (1) along the blade shaft of the ultrasonic scalpel, which is a solution of an equation.

7. A temperature control system for a blade shaft of an ultrasonic scalpel based on a temperature distribution function model, comprising:
  a storage unit, configured to save the temperature distribution function model and at least one threshold value;
  a processing unit, configured to input a corresponding input feature to the temperature distribution function model, and output corresponding temperature data information;
  a comparison unit, configured to compare at least one value in the temperature data information with the threshold value; and
  an adjusting unit, configured to adjust, based on the comparison result, a power level applied to a transducer of the ultrasonic scalpel to modulate the temperature of the blade shaft of the ultrasonic scalpel,
  wherein the temperature distribution function model is a neural network algorithm model, comprising one or a combination of more than one algorithm models of a feedforward neural network, a memory neural network, and an attention neural network; and a training method for the model is one or a combination of more than one of a supervised learning, a semi-supervised learning, an unsupervised learning, and a reinforcement learning, and
  wherein the training method for the model specifically comprises: extracting an input feature from a training set and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing process until the model meets a predetermined stop condition; and stopping training and saving the model after the stop condition is met.

8. A generator for temperature control based on a temperature distribution function model, comprising:
  a control circuit coupled to a memory, wherein the control circuit is configured to be able to:
  save the temperature distribution function model and at least one threshold value;
  input a corresponding input feature to the temperature distribution function model, and output corresponding temperature data information;
  compare at least one value in the temperature data information with the threshold value; and
  adjust, based on the comparison result, a power level applied to a transducer of the ultrasonic scalpel to modulate the temperature of the blade shaft of the ultrasonic scalpel, wherein the temperature distribution function model is a neural network algorithm model, comprising one or a combination of more than one algorithm models of a feedforward neural network, a memory neural network, and an attention neural network; and a training method for the model is one or a combination of more than one of a supervised learning, a semi-supervised learning, an unsupervised learning, and a reinforcement learning, and
  wherein the training method for the model specifically comprises: extracting an input feature from a training set and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing process until the model meets a predetermined stop condition; and stopping training and saving the model after the stop condition is met.

9. The generator according to claim 8, wherein the control circuit is configured that the input feature input to the temperature distribution function model comprises one or a combination of more than one of a working feedback parameter, a physical structure feature parameter, and an environmental parameter.

10. The generator according to claim 9, wherein the working feedback parameter comprises, but is not limited to a real-time voltage U, a real-time current I, a power P, an impedance R, and a real-time response frequency f; the physical structure feature parameter comprises, but is not limited to a material of the blade shaft of the ultrasonic scalpel, and a length of the blade shaft; and
  the environmental parameter comprises, but is not limited to an environmental temperature, and an environmental humidity.

11. The generator according to claim 8, wherein the temperature data information comprises a real-time temperature value at any point on the blade shaft of the ultrasonic scalpel, and/or a maximum temperature value, a minimum temperature value, and an average temperature of a certain area on the blade shaft of the ultrasonic scalpel.

12. An ultrasonic scalpel surgical instrument based on a temperature distribution function model, comprising:
  an ultrasonic electromechanical system, comprising an ultrasonic transducer connected to an ultrasonic scalpel through an ultrasonic waveguide; and
  a generator, configured to supply power to the ultrasonic transducer, wherein the generator comprises a control circuit configured to be able to:
  save the temperature distribution function model and at least one threshold value;
  input a corresponding input feature to the temperature distribution function model, and output corresponding temperature data information;
  compare at least one value in the temperature data information with the threshold value; and
  adjust, based on the comparison result, a power level applied to the transducer of the ultrasonic scalpel to modulate the temperature of a blade shaft of the ultrasonic scalpel,
  wherein the temperature distribution function model is a neural network algorithm model, comprising one or a combination of more than one algorithm models of a feedforward neural network, a memory neural network, and an attention neural network; and a training method for the model is one or a combination of more than one of a supervised learning, a semi-supervised learning, an unsupervised learning, and a reinforcement learning, and wherein the training method for the model specifically comprises: extracting an input feature from a training set and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing process until the model meets a predetermined stop condition; and stopping training and saving the model after the stop condition is met.

13. The ultrasonic scalpel surgical instrument according to claim 12, wherein the control circuit is configured that the input feature input to the temperature distribution function model comprises one or a combination of more than one of a working feedback parameter, a physical structure feature parameter, and an environmental parameter; wherein the working feedback parameter comprises, but is not limited to a real-time voltage U, a real-time current I, a power P, an impedance R, and a real-time response frequency f; the physical structure feature parameter comprises, but is not limited to a material of the blade shaft of the ultrasonic scalpel blade, and a length of the blade shaft; and the environmental parameter comprises, but is not limited to an environmental temperature, and an environmental humidity.

14. The ultrasonic scalpel surgical instrument according to claim 12, wherein the temperature data information comprises a real-time temperature value at any point on the blade shaft of the ultrasonic scalpel, and/or a maximum temperature value, a minimum temperature value, and an average temperature of a certain area on the blade shaft of the ultrasonic scalpel.

15. An ultrasonic scalpel system based on a temperature distribution function model, comprising a processor and a non-volatile storage device comprising an application program, wherein the application program, when executed by the processor, enables the processor to:

save the temperature distribution function model and at least one threshold value;

input a corresponding input feature to the temperature distribution function model, and output corresponding temperature data information;

compare at least one value in the temperature data information with the threshold value; and adjust, based on the comparison result, a power level applied to a transducer of the ultrasonic scalpel to modulate the temperature of a blade shaft of the ultrasonic scalpel, wherein the temperature distribution function model is a neural network algorithm model, comprising one or a combination of more than one algorithm models of a feedforward neural network, a memory neural network, and an attention neural network; and a training method for the model is one or a combination of more than one of a supervised learning, a semi-supervised learning, an unsupervised learning, and a reinforcement learning, and wherein the training method for the model specifically comprises: extracting an input feature from a training set and inputting the same into the neural network algorithm model to calculate an intermediate value and a gradient value for each neuron, wherein a loss function of the model is a mean square error MSE or an average absolute error MAE; updating a weight by a gradient descent method; repeating the foregoing process until the model meets a predetermined stop condition; and stopping training and saving the model after the stop condition is met.

16. The ultrasonic scalpel system according to claim 15, wherein the temperature distribution function model consists of layers, corresponding neurons, and weights; wherein weight parameters and the application program are saved in a memory of the generator; the memory comprises a flash, an EEPROM, or another non-volatile storage device; the application program runs in a processor; and the processor comprises an ARM, a DSP, a FPGA, a CPU, a GPU, or an ASIC chip existing in the generator, or is a remote server connected through a network.

* * * * *